US012778617B2

(12) United States Patent
Cao et al.

(10) Patent No.: US 12,778,617 B2
(45) Date of Patent: Nov. 3, 2026

(54) MEDICAL ULTRASONIC SCALPEL, MEDICAL ULTRASONIC SCALPEL SYSTEM, AND ROBOTIC-ASSISTED ULTRASONIC SCALPEL SYSTEM

(71) Applicant: SMTP Medical Co., Ltd., Beijing (CN)

(72) Inventors: Qun Cao, Beijing (CN); Songtao Zhan, Beijing (CN); Zhiling Dai, Beijing (CN)

(73) Assignee: SMTP Medical Co., Ltd., Beijing (CN)

( * ) Notice: Subject to any disclaimer, the term of this patent is extended or adjusted under 35 U.S.C. 154(b) by 0 days.

(21) Appl. No.: 18/859,052

(22) PCT Filed: Apr. 6, 2023

(86) PCT No.: PCT/CN2023/086623
§ 371 (c)(1),
(2) Date: Oct. 22, 2024

(87) PCT Pub. No.: WO2023/216778
PCT Pub. Date: Nov. 16, 2023

(65) Prior Publication Data

US 2025/0204945 A1 Jun. 26, 2025

(30) Foreign Application Priority Data

May 11, 2022 (CN) ......................... 202210515289.5
May 11, 2022 (CN) ........................ 202221138828.X

(51) Int. Cl.
*A61B 17/32* (2006.01)
*A61B 17/16* (2006.01)

(52) U.S. Cl.
CPC .. *A61B 17/320068* (2013.01); *A61B 17/1628* (2013.01); *A61B 2017/320075* (2017.08); *A61B 2017/320098* (2017.08)

(58) Field of Classification Search
CPC ............ A61B 17/320068; A61B 2017/320093
See application file for complete search history.

(56) References Cited

U.S. PATENT DOCUMENTS 6,283,981 B1 * 9/2001 Beaupre ......... A61B 17/320068 606/169
6,423,082 B1 * 7/2002 Houser .......... A61B 17/320068 606/169

(Continued)

FOREIGN PATENT DOCUMENTS

AU 2005218499 B2 9/2005
CN 101394799 A 3/2009

(Continued)

OTHER PUBLICATIONS

Extended European Search Report (EESR) of counterpart application 23802554.8, Jun. 25, 2026, 16 pages, European Patent Office (EPO), Munich, Germany.

*Primary Examiner* — Zade Coley
(74) *Attorney, Agent, or Firm* — Mark P. Mathison

(57) ABSTRACT

The present application provides a medical ultrasonic scalpel, a medical ultrasonic scalpel system, and a robotic-assisted ultrasonic scalpel system, and relates to the technical field of medical instruments. In the medical ultrasonic scalpel, a composite vibration pattern generating portion is provided on at least one of a handle and a shank and can, under the action of a vibration source, drive a blade to generate a composite vibration including at least two of a longitudinal vibration, a torsional vibration and a bending vibration, such that the medical ultrasonic scalpel can generate a variety of vibrations to adapt to various types of surgeries, thereby improving the scope of application of the medical ultrasonic scalpel in surgery.

14 Claims, 12 Drawing Sheets

(56) References Cited

U.S. PATENT DOCUMENTS

| | | | | |
|---|---|---|---|---|
| 8,663,223 | B2 * | 3/2014 | Masuda | A61B 17/320092 606/169 |
| 11,684,375 | B2 * | 6/2023 | Cao | A61B 17/1604 606/80 |
| 2002/0138090 | A1 | 9/2002 | Jewett | |
| 2003/0125620 | A1 | 7/2003 | Satou et al. | |
| 2003/0212331 | A1 | 11/2003 | Fenton et al. | |
| 2005/0234484 | A1 * | 10/2005 | Houser | A61B 17/22012 606/167 |
| 2006/0036180 | A1 | 2/2006 | Boukhny et al. | |
| 2008/0188878 | A1 * | 8/2008 | Young | A61B 17/144 606/171 |
| 2009/0270891 | A1 * | 10/2009 | Beaupre | A61B 17/320092 606/169 |
| 2014/0316415 | A1 * | 10/2014 | Young | A61B 17/16 606/84 |
| 2016/0045770 | A1 * | 2/2016 | Yamada | A61B 18/1445 601/2 |
| 2018/0008303 | A1 | 1/2018 | Wuchinich | |
| 2019/0223899 | A1 * | 7/2019 | Pretorius | B23K 26/142 |
| 2020/0305892 | A1 * | 10/2020 | Cao | A61B 17/320068 |
| 2020/0305922 | A1 * | 10/2020 | Yan | A61B 17/320068 |
| 2021/0228228 | A1 | 7/2021 | Witt et al. | |
| 2021/0393286 | A1 | 12/2021 | Gras et al. | |
| 2022/0265304 | A1 * | 8/2022 | Akagane | A61B 17/320092 |
| 2024/0197354 | A1 * | 6/2024 | Cowley | A61B 17/320068 |

FOREIGN PATENT DOCUMENTS

| | | | | | |
|---|---|---|---|---|---|
| CN | 104066391 | A | * | 9/2014 | B06B 3/00 |
| CN | 104349737 | A | | 2/2015 | |
| CN | 105310746 | A | | 2/2016 | |
| CN | 108024822 | A | | 5/2018 | |
| CN | 110141308 | A | | 8/2019 | |
| CN | 114886513 | A | | 8/2022 | |
| CN | 217408915 | U | | 9/2022 | |
| CN | 115500900 | A | * | 12/2022 | A61B 17/320068 |
| DE | 212018000162 | U1 | | 1/2020 | |
| EP | 3721819 | A1 | | 10/2020 | |
| JP | 2004275592 | A | | 10/2004 | |
| JP | 2019528896 | A | | 10/2019 | |
| JP | 2020518350 | A | | 6/2020 | |
| JP | 2020131004 | A2 | | 8/2020 | |
| WO | 03/095028 | A1 | | 11/2003 | |
| WO | 2008/154338 | A1 | | 12/2008 | |
| WO | 2009/111436 | A2 | | 9/2009 | |
| WO | WO-2015029518 | A1 | * | 3/2015 | A61B 18/1445 |
| WO | WO-2019062348 | A1 | * | 4/2019 | A61B 17/1604 |

* cited by examiner

10

MEDICAL ULTRASONIC SCALPEL, MEDICAL ULTRASONIC SCALPEL SYSTEM, AND ROBOTIC-ASSISTED ULTRASONIC SCALPEL SYSTEM

CROSS-REFERENCE TO RELATED APPLICATIONS

This application is a U.S. National Stage of International Application No. PCT/CN2023/086623, filed on Apr. 6, 2023, which claims the benefit of Chinese Patent Application No. 202210515289.5, and No. 202221138828.X titled "MEDICAL ULTRASONIC SCALPEL, MEDICAL ULTRASONIC SCALPEL SYSTEM, AND ROBOTIC-ASSISTED ULTRASONIC SCALPEL SYSTEM" filed on May 11, 2022. The contents of the applications are hereby incorporated by reference in their entireties for all purposes.

TECHNICAL FIELD

The present application relates to the field of medical instruments, and in particular to a medical ultrasonic scalpel, a medical ultrasonic scalpel system and a robotic-assisted ultrasonic scalpel system.

BACKGROUND ART

In modern medicine, common surgical tools include medical high-speed grinding drills, oscillating saws and other conventional tools. Bone cutting, drilling, or grinding can be performed with surgical tools to achieve the purpose of bone treatment.

However, in the actual use of surgical tools, especially when a surgical site is close to an interface between a bone and a soft tissue (especially the spinal cord), it is difficult to ensure that conventional surgical tools such as high-speed grinding drills and oscillating saws will treat the bone without damaging the soft tissue. Specifically, it is difficult for medical high-speed grinding drills to accurately control the depth of bone drilling, and it is likely to damage the soft tissue while drilling the bone; and the oscillating saws are not only difficult to control accurately due to large oscillation amplitude, but also likely to accidentally damage the soft tissue near the bone.

With the development of ultrasound technology and its combination with modern medicine, medical ultrasonic scalpels are gradually applied in surgical operations. Moreover, due to the characteristics of ultrasound, when a medical ultrasonic scalpel comes into contact with a bone with a high hardness, the bone is less likely to be deformed, so that cutting can be produced at the contact position. When the medical ultrasonic scalpel comes into contact with the soft tissue, the soft tissue will be bounced or deformed under the elastic action of the soft tissue, and will vibrate slightly with the vibration of the medical ultrasonic scalpel, thereby offsetting the energy at a blade and avoiding cutting. Therefore, especially for surgical operations where the surgical site is located near the interface between the bone and the soft tissue, the medical ultrasonic scalpel has significant advantages in bone cutting.

On this basis, how to take advantage of the medical ultrasonic scalpel so that it can replace conventional surgical tools and be widely used in a variety of surgical types has gradually become a research hotspot.

SUMMARY OF THE INVENTION

The present application is intended to solve at least one of the technical problems existing in the related art. To this end, it is an objective of the present application to propose a medical ultrasonic scalpel, a medical ultrasonic scalpel system and a robotic-assisted ultrasonic scalpel system, to improve the scope of application of the medical ultrasonic scalpel in surgery.

In a first aspect, an embodiment of the present application provides a medical ultrasonic scalpel, including: a handle having a handle longitudinal central axis, a first end of the handle being configured to be connected to a vibration source to receive a vibration generated by the vibration source; a shank having a shank longitudinal central axis, a first end of the shank being connected to a second end of the handle opposite to the first end of the handle; a blade having a blade longitudinal central axis, a first end of the blade being connected to a second end of the shank opposite to the first end of the shank, and a second end of the blade being provided with a cutting portion for cutting a tissue to be cut; and a composite vibration pattern generating portion provided on at least one of the handle and the shank and configured to convert the vibration received from the vibration source into a composite vibration of the cutting portion of the blade, the composite vibration including at least two of the following vibrations: a longitudinal vibration parallel to at least one of the handle longitudinal central axis, the shank longitudinal central axis and the blade longitudinal central axis; a torsional vibration with at least one of the handle longitudinal central axis, the shank longitudinal central axis and the blade longitudinal central axis as a torsional central axis; and a bending vibration laterally offset from at least one of the handle longitudinal central axis, the shank longitudinal central axis and the blade longitudinal central axis.

In a second aspect, an embodiment of the present application provides a medical ultrasonic scalpel system, including a vibration source and a medical ultrasonic scalpel as described above, wherein the vibration source is connected to a first end of a handle of the medical ultrasonic scalpel, and is configured to generate a vibration.

In a third aspect, an embodiment of the present application provides a robotic-assisted ultrasonic scalpel system, including: a robotic-assisted surgical device and a medical ultrasonic scalpel system as described above, wherein the robotic-assisted surgical device is connected to a medical ultrasonic scalpel of the medical ultrasonic scalpel system to control movement of the medical ultrasonic scalpel.

In the medical ultrasonic scalpel, the medical ultrasonic scalpel system, and the robotic-assisted ultrasonic scalpel system provided in the embodiments of the present application, the composite vibration pattern generating portion is provided on at least one of the handle and the shank and can, under the action of a vibration source, drive a blade to generate a composite vibration including at least two of a longitudinal vibration, a torsional vibration and a bending vibration, such that the medical ultrasonic scalpel can generate a variety of vibrations to adapt to various types of surgeries, thereby improving the scope of application of the medical ultrasonic scalpel in surgery.

BRIEF DESCRIPTION OF THE DRAWINGS

In the accompanying drawings, the same reference signs denote the same or similar components or elements throughout a plurality of accompanying drawings unless otherwise specified. These accompanying drawings are not necessarily drawn to scale. It should be understood that these drawings depict only some embodiments according to the present disclosure herein and are not to be construed as limiting the scope of the present application.

LIST OF REFERENCE SIGNS

| | |
|---|---|
| 10: medical ultrasonic scalpel; | 100: handle; |
| 200: shank; | 300: blade; |
| 310: cutting portion; | 400: composite vibration pattern generating portion; |
| 410: first composite vibration pattern generating portion; | 411: inclined groove; |
| 420: second composite vibration pattern generating portion; | 421: lateral cutout; |
| 500: conical transition section; | 60: vibration source. |

DETAILED DESCRIPTION OF EMBODIMENTS

Only some exemplary embodiments are briefly described below. As can be appreciated by those skilled in the art, the described embodiments can be modified in various ways without departing from the spirit or scope of the present application. Accordingly, the accompanying drawings and the description are considered as illustrative in nature, rather than limited.

Figure 1:
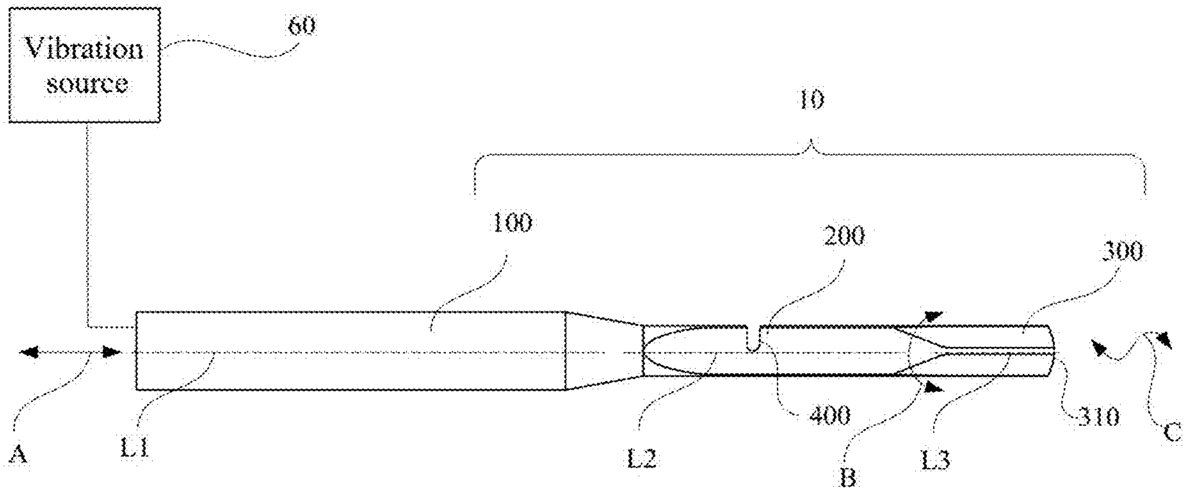
FIG. 1 shows a structural diagram of a medical ultrasonic scalpel system according to an embodiment of the present application.

FIG. 1 shows a structural diagram of a medical ultrasonic scalpel system according to an embodiment of the present application. Referring to FIG. 1, the medical ultrasonic scalpel system includes a medical ultrasonic scalpel 10 and a vibration source 60. The medical ultrasonic scalpel 10 includes: a handle 100, a shank 200, a blade 300 and a composite vibration pattern generating portion 400.

The handle 100 may be of a rod-like structure, and its cross-section may be in various shapes such as round or square. The handle 100 has a handle longitudinal central axis L1, and two opposite ends of the handle 100 along the handle longitudinal central axis L1 are a first end (left end in FIG. 1) and a second end (right end in FIG. 1) of the handle 100, respectively. The first end of the handle 100 may be connected to the vibration source 60 to receive a vibration generated by the vibration source 60.

The shank 200 may be of an elongated strip-like structure, and its cross-section may be in various shapes such as square or oval. The shank 200 has a shank longitudinal central axis L2, and two opposite ends of the shank 200 along the shank longitudinal central axis L2 are a first end (left end in FIG. 1) and a second end (right end in FIG. 1) of the shank 200, respectively. The first end of the shank 200 is connected to the second end of the handle 100.

The blade 300 may also be of an elongated strip-like structure, and its cross-section may be substantially in various shapes such as cross or diamond shapes. The blade 300 has a blade longitudinal central axis L3, and two opposite ends of the blade 300 along the blade longitudinal central axis L3 are a first end (left end in FIG. 1) and a second end (right end in FIG. 1) of the blade 300, respectively. The first end of the blade 300 is connected to the second end of the shank 200, and the second end of the blade 300 is provided with a cutting portion 310 for cutting a tissue to be cut.

The tissue to be cut may be a bone, a blood vessel, and other tissues that need to be treated. For ease of explanation, the following description is given assuming that the tissue to be cut is a bone. The cutting portion 310 may be located at the second end of the blade 300 facing away from the handle 100, and the cutting portion 310 may first come into contact with the bone during surgery to treat the bone.

It can be understood that the handle 100, the shank 200 and the blade 300 may be connected in a sequence generally in a direction from left to right of FIG. 1. In some embodiments, the handle 100 may be of a cylindrical structure, and the shank 200 may be of a sheet-like structure. The cross-section of the shank 200 is substantially in the shape of a rectangle, and the cross-section of the blade 300 may be substantially in the shape of a diamond. Moreover, among the three, the cross-sectional area of the handle 100 is the largest, the cross-sectional area of the blade 300 is the smallest, and the cross-sectional area of the shank 200 is between that of the handle 100 and that of the blade 300.

In addition, the relationship between the handle longitudinal central axis L1, the shank longitudinal central axis L2 and the blade longitudinal central axis L3 may be varied.

In some embodiments, the handle longitudinal central axis L1 and the shank longitudinal central axis L2 coincide with each other, and the blade longitudinal central axis L3 is offset by a predetermined distance from, or at a predetermined angle with respect to, the handle longitudinal central axis L1 and the shank longitudinal central axis L2. That is, the handle 100 and the shank 200 may extend in the same direction, and the blade longitudinal central axis L3 may be at a preset angle with respect to the shank longitudinal central axis L2, or the blade longitudinal central axis L3 may be parallel to, and offset by a predetermined distance from, the shank longitudinal central axis L2.

In some other embodiments, the handle longitudinal central axis L1 and the blade longitudinal central axis L3 coincide with each other, and the shank longitudinal central axis L2 is offset by a predetermined distance from, or at a predetermined angle with respect to, the handle longitudinal central axis L1 and the blade longitudinal central axis L3. That is, the handle 100 and the blade 300 may extend in the same direction, and the shank longitudinal central axis L2 may be at a preset angle with respect to the blade longitudinal central axis L3, or the shank longitudinal central axis L2 may be parallel to, and offset by a predetermined distance from, the blade longitudinal central axis L3.

In yet other embodiments, the handle longitudinal central axis L1, the shank longitudinal central axis L2 and the blade longitudinal central axis L3 coincide with one another. The three may be connected in sequence in the same direction.

The above various arrangements may enable the connection of the handle 100, the shank 200, and the blade 300. The preset angle may be greater than 0° and less than 180°, and the preset distance may be set according to the actual requirements.

The medical ultrasonic scalpel 10 further includes a composite vibration pattern generating portion 400. The composite vibration pattern generating portion 400 is provided on at least one of the handle 100 and the shank 200, and the composite vibration pattern generating portion 400 is configured to convert the vibration received from the vibration source 60 into a composite vibration of the cutting portion 310 of the blade 300. The composite vibration includes at least two of the following vibrations:

1) A longitudinal vibration parallel to at least one of the handle longitudinal central axis L1, the shank longitudinal central axis L2 and the blade longitudinal central axis L3. Taking the longitudinal vibration parallel to the blade longitudinal central axis L3 as an example, the longitudinal vibration may cause the length of the medical ultrasonic scalpel 10 to change back and forth in a first direction A (in the direction of L3).
2) A torsional vibration with at least one of the handle longitudinal central axis L1, the shank longitudinal central axis L2 and the blade longitudinal central axis L3 as a torsional central axis. Taking the blade longitudinal central axis L3 as the torsional central axis as an example, the torsional vibration may cause the medical ultrasonic scalpel 10 to rotate back and forth in a second direction B.
3) A bending vibration laterally offset from at least one of the handle longitudinal central axis L1, the shank longitudinal central axis L2 and the blade longitudinal central axis L3. Taking the bending vibration offset from the blade longitudinal central axis L3 as an example, the bending vibration may cause the medical ultrasonic scalpel 10 to bend and deform in a third direction C.

It can be understood that the composite vibration may include at least two of the longitudinal vibration, the torsional vibration, and the bending vibration. A combination of the longitudinal vibration and the torsional vibration may simulate the motion of a high-speed grinding drill or an oscillating saw, to realize the bone drilling or grinding treatment, and a combination of longitudinal motion and bending motion may simulate the motion of an oscillating saw or an osteotome, to realize the bone grinding or cutting treatment. A combination of the torsional vibration and the bending vibration may also realize the bone drilling or grinding treatment. In addition, a combination of the longitudinal vibration, the torsional vibration and the bending vibration may realize the bone drilling, cutting or grinding treatment.

During surgery, the composite vibration mode of the blade 300 may be selected according to the type of surgery to replace conventional surgical tools such as high-speed grinding drills or oscillating saws to treat the bone, so that the medical ultrasonic scalpel 10 can be applied to a variety of different types of surgeries, thereby improving the scope of application of the medical ultrasonic scalpel in surgery. Moreover, the surgery performed with the medical ultrasonic scalpel 10 will not cause damage to the soft tissue near the bone and is highly safe.

It can be understood that the composite vibration of the blade 300 can be realized in a variety of ways. For example, the structure of the medical ultrasonic scalpel 10 may be configured by means of the composite vibration pattern generating portion 400 such that the medical ultrasonic scalpel 10 converts a single type of vibration generated by the vibration source 60 into a composite vibration. For another example, the vibration source 60 may be configured such that the vibration source 60 may provide a variety of types of vibrations to the medical ultrasonic scalpel 10. In this case, the composite vibration pattern generating portion 400 may be formed by at least part of the handle 100 and the shank 200.

The method of generating the composite vibration is explained below in conjunction with the accompanying drawings.

Figure 2:
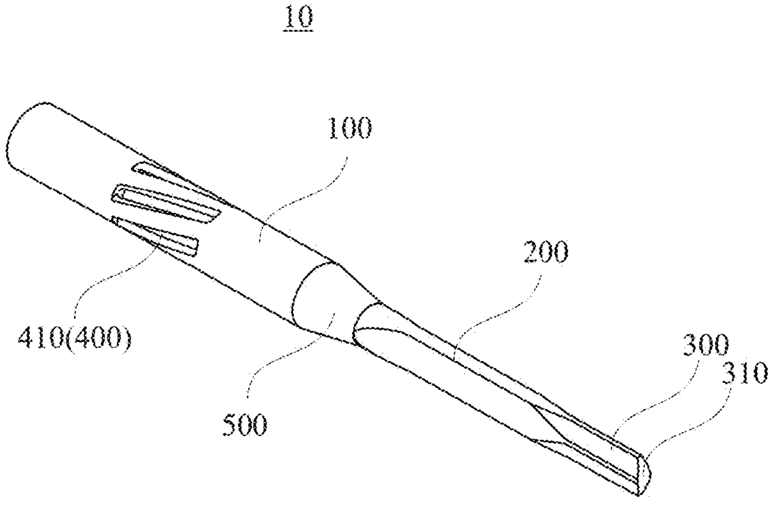
FIG. 2 shows a schematic structural diagram of a medical ultrasonic scalpel according to an embodiment of the present application.
Figure 3:
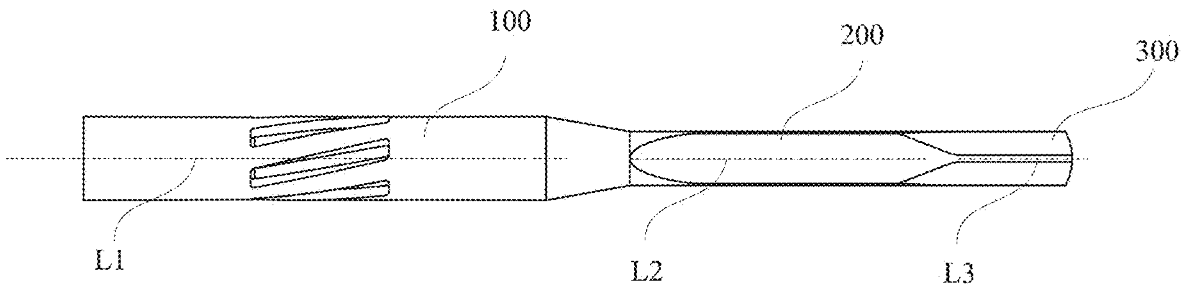
FIG. 3 is a front view of the medical ultrasonic scalpel of FIG. 2.
Figure 4:
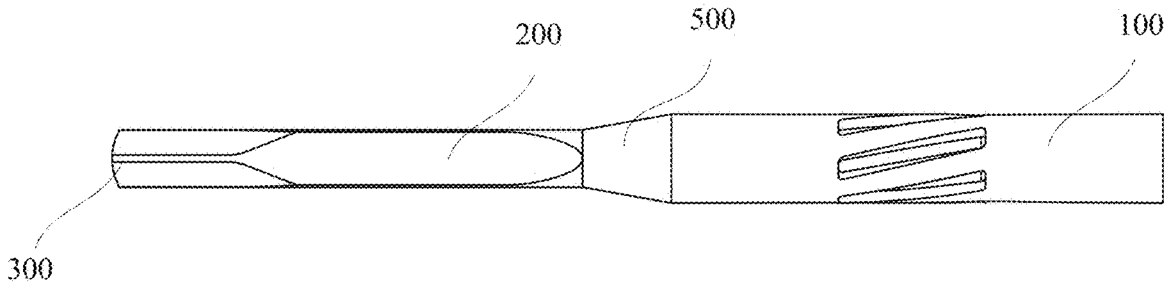
FIG. 4 is a rear view of the medical ultrasonic scalpel of FIG. 2.
Figure 5:
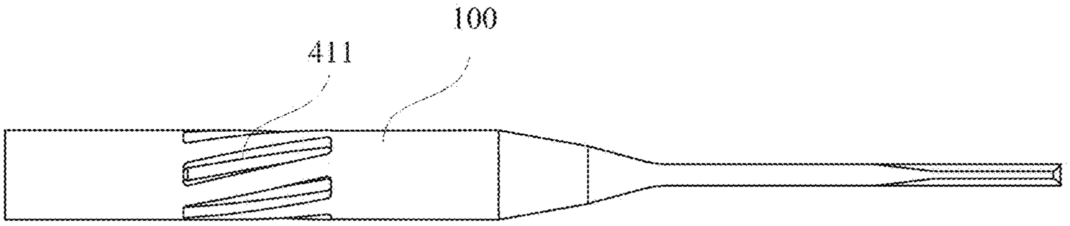
FIG. 5 is a top view of the medical ultrasonic scalpel of FIG. 2.
Figure 6:
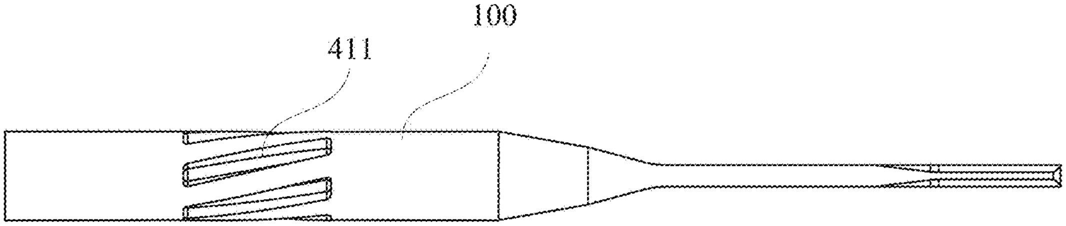
FIG. 6 is a bottom view of the medical ultrasonic scalpel of FIG. 2.
Figure 7:
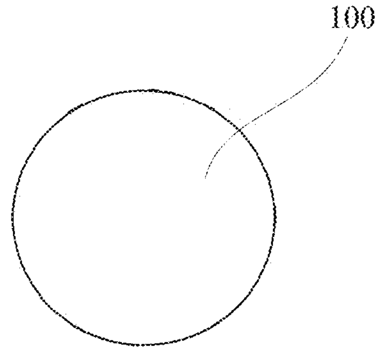
FIG. 7 is a left side view of the medical ultrasonic scalpel of FIG. 2.
Figure 8:
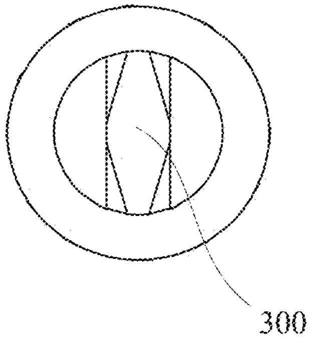
FIG. 8 is a right side view of the medical ultrasonic scalpel of FIG. 2.

FIG. 2 shows a schematic structural diagram of a medical ultrasonic scalpel according to an embodiment of the present application; FIG. 3 is a front view of the medical ultrasonic scalpel of FIG. 2; FIG. 4 is a rear view of the medical ultrasonic scalpel of FIG. 2; FIG. 5 is a top view of the medical ultrasonic scalpel of FIG. 2; FIG. 6 is a bottom view of the medical ultrasonic scalpel of FIG. 2; FIG. 7 is a left side view of the medical ultrasonic scalpel of FIG. 2; and FIG. 8 is a right side view of the medical ultrasonic scalpel of FIG. 2.

Referring to FIGS. 2 to 8, the vibration source 60 may generate a longitudinal vibration. The composite vibration pattern generating portion 400 includes a first composite vibration pattern generating portion 410 provided in the handle 100. The first composite vibration pattern generating portion 410 is configured to convert a longitudinal vibration component of the vibration source 60 into the torsional vibration, so that the composite vibration (the superposition of the longitudinal vibration and the torsional vibration) of the cutting portion 310 of the blade 300 can be realized by configuring the structure of the medical ultrasonic scalpel 10.

The first composite vibration pattern generating portion 410 may be of various structures. For example, the first composite vibration pattern generating portion 410 may be a groove provided on the handle 100.

With continued reference to FIG. 5, the first composite vibration pattern generating portion 410 includes at least one inclined groove 411 provided on an outer periphery of the handle 100 at a first predetermined included angle with respect to the handle longitudinal central axis L1. The inclined groove 411 may be at the first predetermined included angle with respect to the handle longitudinal central axis L1. That is, an extension direction of the inclined groove 411 is not parallel to the handle longitudinal central axis L1.

In addition, there may be one or more inclined grooves 411. When there are a plurality of inclined grooves 411, the at least one inclined groove 411 includes two or more inclined grooves 411 evenly distributed along the outer periphery of the handle 100. That is, the plurality of inclined grooves 411 may be equally spaced along the outer periphery of the handle 100. The first predetermined included angle may be greater than 0° and less than 180°.

When the vibration source 60 generates a longitudinal vibration, part of the longitudinal vibration component of the longitudinal vibration acts on the first composite vibration pattern generating portion 410. Since the inclined groove 411 is at the first predetermined included angle with respect to the handle longitudinal central axis L1, the part of the longitudinal vibration component is converted into the torsional vibration for rotation along the circumferential direction of the handle 100, so as to drive the cutting portion 310 to realize the torsional vibration. Moreover, since there is still part of the longitudinal vibration component that is not converted to the torsional vibration, the cutting portion 310 can still generate a longitudinal vibration under the action of the vibration source 60. That is, the cutting portion 310 of the blade 300 can realize a composite vibration of the longitudinal vibration and the torsional vibration.

In some embodiments, the first composite vibration pattern generating portion 410 may include at least one helical groove provided on the outer periphery of the handle 100 at the first predetermined included angle with respect to the handle longitudinal central axis L1. The helical groove may extend in the direction of a helix, and the first predetermined included angle may be a helix angle of the helix.

In addition, there may be one or more helical grooves. When there are a plurality of helical grooves, there are a plurality of helical grooves, the at least one helical groove includes two or more helical grooves evenly distributed along the outer periphery of the handle 100. That is, the plurality of helical grooves are arranged at intervals in the circumferential direction of the handle 100.

Of course, the first composite vibration pattern generating portion 410 may alternatively include both at least one inclined groove 411 and at least one helical groove, and also enable the cutting portion 310 to realize a composite vibration of the longitudinal vibration and the torsional vibration. That is, the at least one inclined groove and the at least one helical groove include two or more inclined grooves and two or more helical grooves, respectively, evenly distributed along the outer periphery of the handle 100.

In addition to being a groove provided on the handle 100, the first composite vibration pattern generating portion 410 may be provided as a protrusion on the handle 100.

For example, the first composite vibration pattern generating portion 410 is at least one strip-like protrusion provided on the outer periphery of the handle 100 at the first predetermined included angle with respect to the handle longitudinal central axis L1. The inclined groove 411 may be at the first predetermined included angle with respect to the handle longitudinal central axis L1. That is, an extension direction of the strip-like protrusion is not parallel to the handle longitudinal central axis L1.

In addition, there may be one or more strip-like protrusions. A plurality of strip-like protrusions may be equally spaced along the outer periphery of the handle 100. The first predetermined included angle may be greater than 0° and less than 180°.

When the vibration source 60 generates a longitudinal vibration, part of the longitudinal vibration component of the longitudinal vibration acts on the first composite vibration pattern generating portion 410. Since the strip-like protrusion is at the first predetermined included angle with respect to the handle longitudinal central axis L1, the part of the longitudinal vibration component is converted into the torsional vibration for rotation along the circumferential direction of the handle 100, so as to drive the cutting portion 310 to realize the torsional vibration. Moreover, since there is still part of the longitudinal vibration component that is not converted to the torsional vibration, the cutting portion 310 can still generate a longitudinal vibration under the action of the vibration source 60. That is, the cutting portion 310 of the blade 300 can realize a composite vibration of the longitudinal vibration and the torsional vibration.

For another example, the first composite vibration pattern generating portion 410 is a helical protrusion provided on the outer periphery of the handle 100 at the first predetermined included angle with respect to the handle longitudinal central axis L1. The helical protrusion may extend in the direction of a helix, and the first predetermined included angle may be a helix angle of the helix.

In addition, there may be one or more helical protrusions. When there are a plurality of helical protrusions, the plurality of helical grooves may be arranged at intervals along the handle longitudinal central axis L1, or along the circumferential direction of the handle 100.

For still another example, the first composite vibration pattern generating portion 410 may alternatively include both at least one strip-like protrusion and at least one helical protrusion, and also enable the cutting portion 310 to realize a composite vibration of the longitudinal vibration and the torsional vibration.

Of course, in some other embodiments, the first composite vibration pattern generating portion 410 may include both the grooves and the protrusions provided on the handle 100.

The above various structures of the first composite vibration pattern generating portion 410 can all convert the longitudinal vibration component into the torsional vibration, such that the cutting portion 310 realizes the composite vibration of the longitudinal vibration and the torsional vibration.

Figure 9:
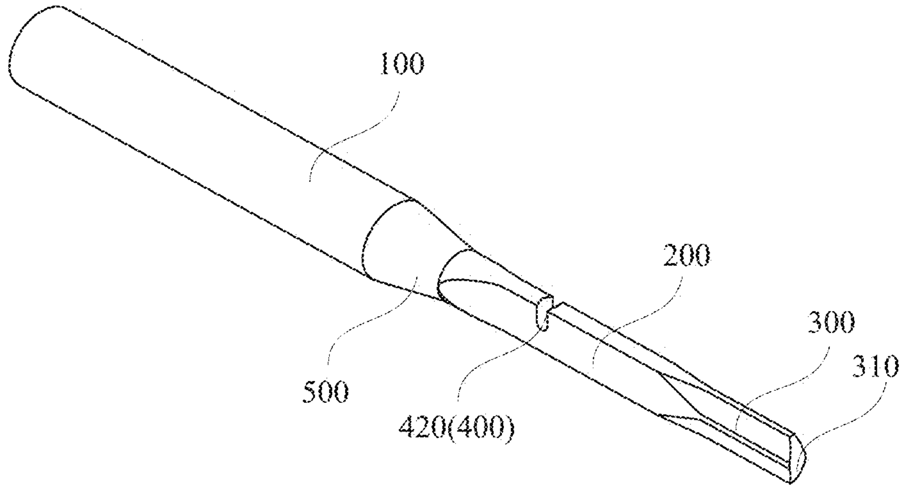
FIG. 9 shows a schematic structural diagram of a medical ultrasonic scalpel according to another embodiment of the present application.
Figure 10:
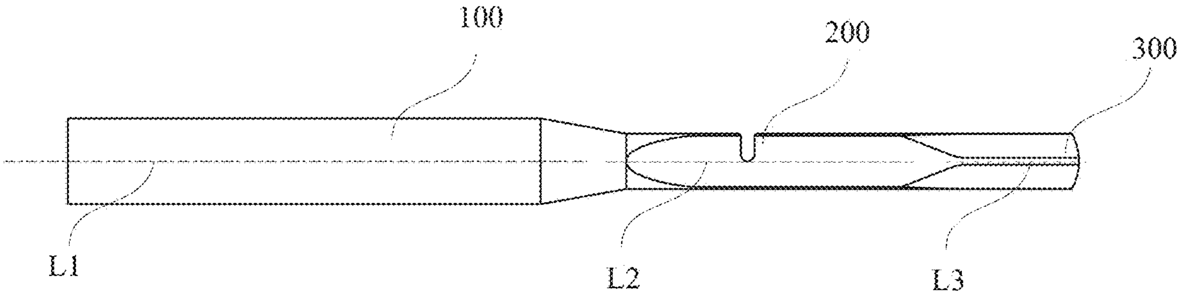
FIG. 10 is a front view of the medical ultrasonic scalpel of FIG. 9.
Figure 11:
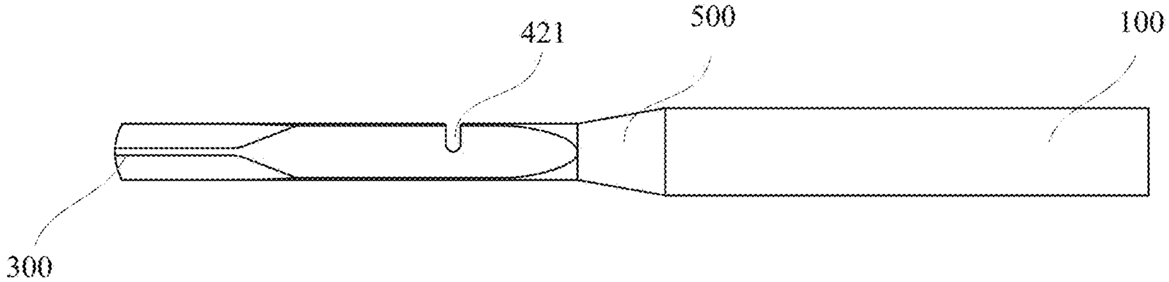
FIG. 11 is a rear view of the medical ultrasonic scalpel of FIG. 9.
Figure 12:
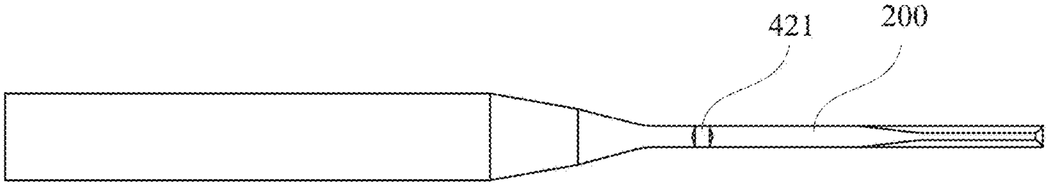
FIG. 12 is a top view of the medical ultrasonic scalpel of FIG. 9.
Figure 13:
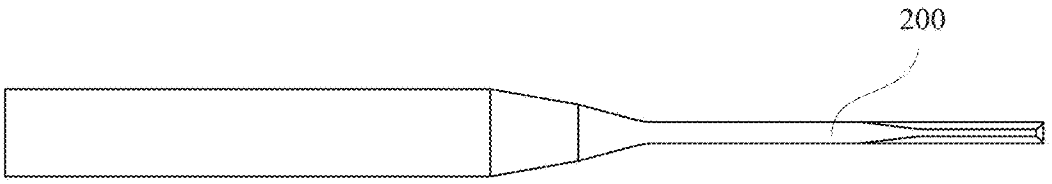
FIG. 13 is a bottom view of the medical ultrasonic scalpel of FIG. 9.
Figure 14:
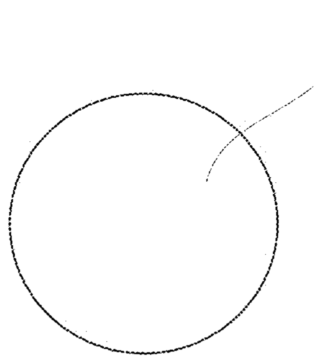
FIG. 14 is a left side view of the medical ultrasonic scalpel of FIG. 9.
Figure 15:
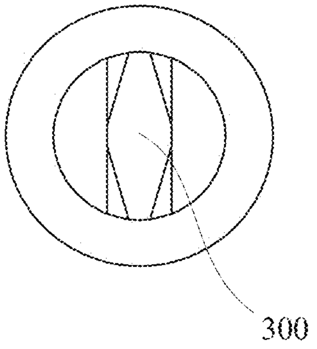
FIG. 15 is a right side view of the medical ultrasonic scalpel of FIG. 9.

FIG. 9 shows a schematic structural diagram of a medical ultrasonic scalpel according to another embodiment of the present application; FIG. 10 is a front view of the medical ultrasonic scalpel of FIG. 9; FIG. 11 is a rear view of the medical ultrasonic scalpel of FIG. 9; FIG. 12 is a top view of the medical ultrasonic scalpel of FIG. 9; FIG. 13 is a bottom view of the medical ultrasonic scalpel of FIG. 9; FIG. 14 is a left side view of the medical ultrasonic scalpel of FIG. 9; and FIG. 15 is a right side view of the medical ultrasonic scalpel of FIG. 9.

Referring to FIGS. 9 to 15, the vibration source 60 may generate a longitudinal vibration. The composite vibration pattern generating portion 400 further includes a second composite vibration pattern generating portion 420 provided in the handle 100 or the shank 200. The second composite vibration pattern generating portion 420 is configured to convert a longitudinal vibration component of the vibration source 60 into the bending vibration, so that the composite vibration (the superposition of the longitudinal vibration and the bending vibration) of the cutting portion 310 of the blade 300 can be realized by configuring the structure of the medical ultrasonic scalpel 10.

The second composite vibration pattern generating portion 420 may also be of various structures, and the second composite vibration pattern generating portion 420 is formed by at least one lateral cutout 421 of the shank 200.

It can be understood that the lateral cutout 421 may be formed by removing a part of material from a side surface of the shank 200, and may be represented as a recess in the shank 200. There may also be one or more lateral cutouts 421, and the lateral cutouts 421 may be such that the shank 200 is of an asymmetric structure. For example, when there are a plurality of lateral cutouts, the plurality of lateral cutouts 421 are arranged at intervals along the longitudinal central axis L2 of the shank 200. The side surface may be understood as a lateral surface located between the first end and the second end of the shank 200.

In some embodiments, the shank 200 is of a flat sheet-like structure, and the lateral cutout 421 may be a notch provided at an edge of the shank 200.

In the embodiment shown in FIG. 9, the second composite vibration pattern generating portion 420 is provided on the shank 200. In other embodiments, the second composite vibration pattern generating portion 420 may be provided on the handle 100. For example, the second composite vibration pattern generating portion 420 is formed by at least one lateral cutout of the handle 100.

In some embodiments, in addition to including the lateral cutout, the second composite vibration pattern generating portion 420 may be formed by at least one lateral projection of the handle 100 or the shank 200. The lateral projection may be formed by adding a material to a side surface of the shank 200, and may be represented as a protruding portion on the shank 200. There may also be one or more lateral projections, and the lateral projections may be such that the shank 200 is of an asymmetric structure. For example, when there are a plurality of lateral projections, the plurality of lateral projections may be arranged at intervals along the longitudinal central axis L2 of the shank 200. The side surface may be understood as a lateral surface located between the first end and the second end of the shank 200.

In addition, the lateral projection may be provided on the handle 100. For example, the second composite vibration pattern generating portion 420 is formed by at least one lateral projection of the handle 100.

When the vibration source 60 generates a longitudinal vibration, part of the longitudinal vibration component of the longitudinal vibration acts on the second composite vibration pattern generating portion 420. Since the handle 100 or the shank 200 has an asymmetrical eccentric structure due to the second composite vibration pattern generating portion 420, the structural forces on two sides of the handle longitudinal central axis L1 or the shank longitudinal central axis L2 are unbalanced, so that the medical ultrasonic scalpel 10 generates a bending vibration, so as to drive the cutting portion 310 to realize the bending vibration. Moreover, since there is still part of the longitudinal vibration component that is not converted to the bending vibration, the cutting portion 310 can still generate a longitudinal vibration under the action of the vibration source 60. That is, the cutting portion 310 of the blade 300 can realize a composite vibration of the longitudinal vibration and the bending vibration.

The above various structures of the second composite vibration pattern generating portion 420 can all convert the longitudinal vibration component into the bending vibration, such that the cutting portion 310 realizes the composite vibration of the longitudinal vibration and the bending vibration.

Figure 16:
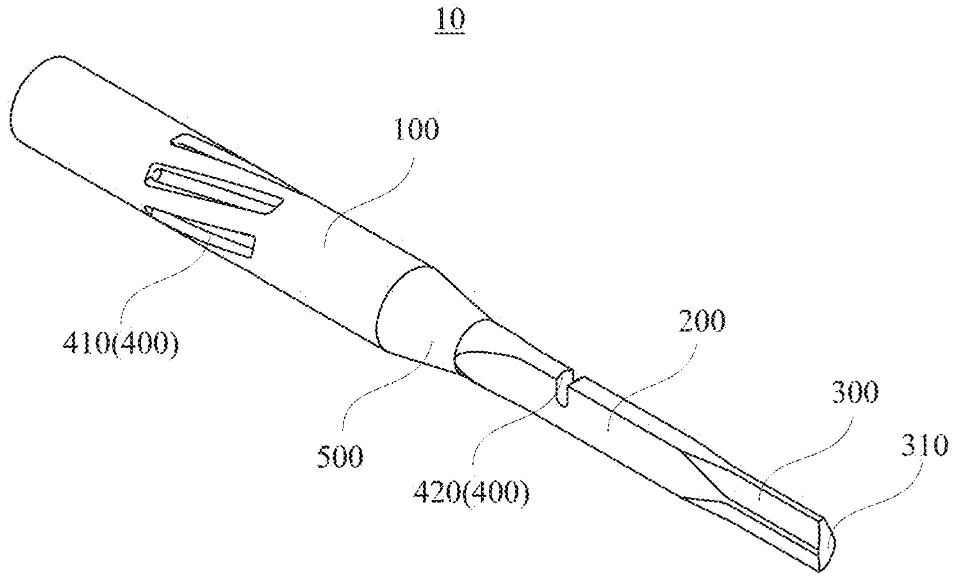
FIG. 16 shows a schematic structural diagram of a medical ultrasonic scalpel according to still another embodiment of the present application.
Figure 17:
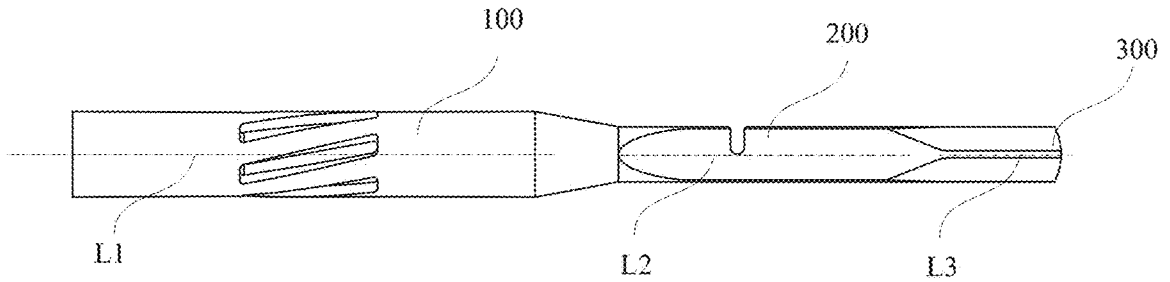
FIG. 17 is a front view of the medical ultrasonic scalpel of FIG. 16.
Figure 18:
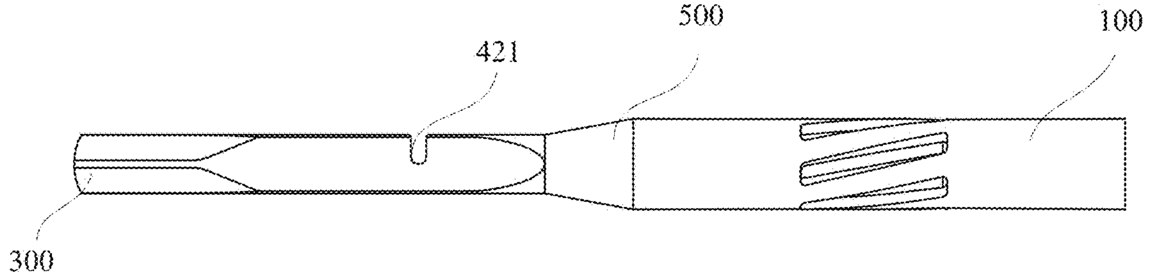
FIG. 18 is a rear view of the medical ultrasonic scalpel of FIG. 16.
Figure 19:
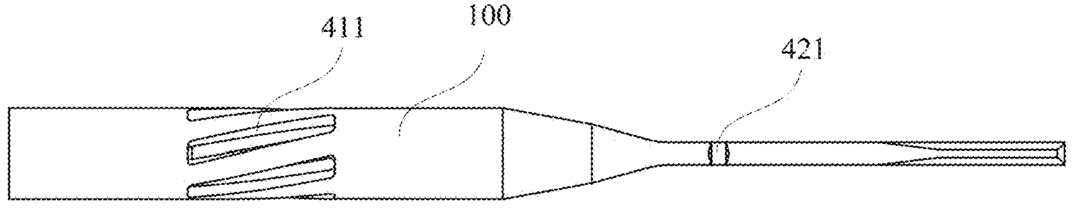
FIG. 19 is a top view of the medical ultrasonic scalpel of FIG. 16.
Figure 20:
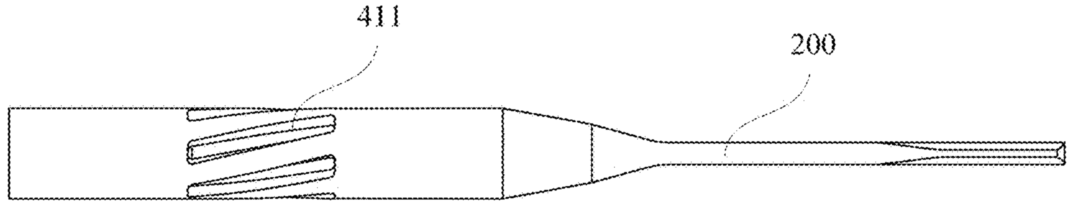
FIG. 20 is a bottom view of the medical ultrasonic scalpel of FIG. 16.
Figure 21:
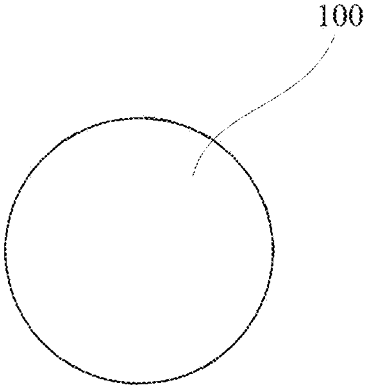
FIG. 21 is a left side view of the medical ultrasonic scalpel of FIG. 16.
Figure 22:
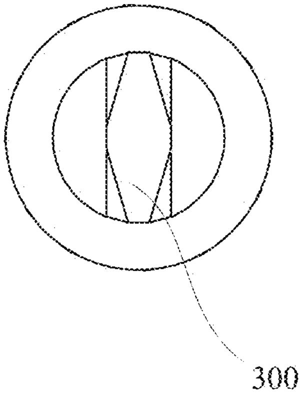
FIG. 22 is a right side view of the medical ultrasonic scalpel of FIG. 16.

FIG. 16 shows a schematic structural diagram of a medical ultrasonic scalpel according to yet another embodiment of the present application; FIG. 17 is a front view of the medical ultrasonic scalpel of FIG. 16; FIG. 18 is a rear view of the medical ultrasonic scalpel of FIG. 16; FIG. 19 is a top view of the medical ultrasonic scalpel of FIG. 16; FIG. 20 is a bottom view of the medical ultrasonic scalpel of FIG. 16; FIG. 21 is a left side view of the medical ultrasonic scalpel of FIG. 16; and FIG. 22 is a right side view of the medical ultrasonic scalpel of FIG. 16.

Referring to FIGS. 16 to 22, this embodiment is based on the embodiment shown in FIG. 2, in conjunction with the embodiment shown in FIG. 9. In this embodiment, the vibration source 60 may generate a longitudinal vibration. The composite vibration pattern generating portion 400 includes a first composite vibration pattern generating portion 410 provided in the handle 100 and a second composite vibration pattern generating portion 420 provided in the handle 100 or the shank 200. The first composite vibration pattern generating portion 410 is configured to convert the longitudinal vibration component of the vibration source 60 into the torsional vibration, and the second composite vibration pattern generating portion 420 is configured to convert the longitudinal vibration component of the vibration source 60 into the bending vibration, so that the composite vibration (the superposition of the longitudinal vibration, the torsional vibration and the bending vibration) of the cutting portion 310 of the blade 300 can be realized by configuring the structure of the medical ultrasonic scalpel 10.

The structures and functions of the first composite vibration pattern generating portion 410 and the second composite vibration pattern generating portion 420 are the same as or similar to those in the above respective embodiments, and will not be described in more detail, and reference may be made specifically to the above embodiments.

When the vibration source 60 generates a longitudinal vibration, the longitudinal vibration may substantially include three parts of the longitudinal vibration component. A part of the longitudinal vibration component acts on the first composite vibration pattern generating portion 410. Since the first composite vibration pattern generating portion 410 is at the first predetermined included angle with respect to the handle longitudinal central axis L1, the part of the longitudinal vibration component is converted into the torsional vibration for rotation along the circumferential direction of the handle 100, so as to drive the cutting portion 310 to realize the torsional vibration.

A second part of the longitudinal vibration component acts on the second composite vibration pattern generating portion 420. Since the handle 100 or the shank 200 has an asymmetrical eccentric structure due to the second composite vibration pattern generating portion 420, the structural forces on two sides of the handle longitudinal central axis L1 or the shank longitudinal central axis L2 are unbalanced, so that the medical ultrasonic scalpel 10 generates a bending vibration, so as to drive the cutting portion 310 to realize the bending vibration.

A third part of the longitudinal vibration component is not converted to the torsional vibration or the bending vibration, so that the cutting portion 310 can still generate a longitudinal vibration under the action of the vibration source 60.

In summary, the composite vibration pattern generating portion 400 enables the cutting portion 310 of the blade 300 to realize a composite vibration including the longitudinal vibration, the bending vibration and the torsional vibration.

In some embodiments, a transverse dimension of the handle 100 is greater than a transverse dimension of the shank 200, that is, the cross-sectional area of the handle 100 is greater than the cross-sectional area of the shank 200, and the second end of the handle 100 is connected to the first end of the shank 200 via a conical transition section 500. The conical transition section 500 can allow for a smooth transition between the handle 100 and the shank 200, increasing the strength of the medical ultrasonic scalpel 10.

The composite vibration pattern generating portion 400 further includes a third composite vibration pattern generating portion provided in the conical transition section 500. The third composite vibration pattern generating portion is configured to convert a longitudinal vibration component of the vibration source 60 into the torsional vibration.

The third composite vibration pattern generating portion may be of various structures. For example, the third composite vibration pattern generating portion may be a groove provided on the conical transition section 500.

For example, the third composite vibration pattern generating portion includes at least one inclined groove provided on the outer periphery of the handle 100 at a second predetermined included angle with respect to the handle longitudinal central axis L1. The inclined groove may be at the second predetermined included angle with respect to the handle longitudinal central axis L1. That is, an extension direction of the inclined groove is not parallel to the handle longitudinal central axis L1. The inclined groove of the third composite vibration pattern generating portion differs from the inclined groove shown in FIG. 2 in that the inclined groove of the third composite vibration pattern generating portion is provided on a conical surface, and the distance between the inclined groove and a central line of the conical transition section 500 gradually decreases in a taper direction of the conical surface, whereas the inclined groove shown in FIG. 2 is provided on a cylindrical surface, and the distance between the inclined groove and the handle longitudinal central axis L1 is constant. The second predetermined included angle may be greater than 0° and less than 180°, which may be the same as or different from the first predetermined included angle.

For another example, the third composite vibration pattern generating portion may include at least one helical groove provided on the outer periphery of the handle 100 at the second predetermined included angle with respect to the handle longitudinal central axis L1. The helical groove may extend in the direction of a conical helix, and the first predetermined included angle may be a helix angle of the conical helix.

Of course, the third composite vibration pattern generating portion may alternatively include both at least one inclined groove and at least one helical groove, and also enable the cutting portion 310 to realize a composite vibration of the longitudinal vibration and the torsional vibration. That is, the at least one inclined groove and the at least one helical groove include two or more inclined grooves and two or more helical grooves, respectively, evenly distributed along the outer periphery of the conical transition section 500.

In addition to being a groove provided on the conical transition section 500, the third composite vibration pattern generating portion may be provided as a protrusion on the conical transition section 500.

For example, the third composite vibration pattern generating portion is at least one strip-like protrusion provided on the outer periphery of the handle 100 at the second predetermined included angle with respect to the handle longitudinal central axis L1. The strip-like protrusion may be at the second predetermined included angle with respect to the handle longitudinal central axis L1. That is, an extension direction of the strip-like protrusion is not parallel to the handle longitudinal central axis L1. Moreover, the distance between the strip-like protrusion and the central line of the conical transition section 500 gradually decreases in the taper direction of the conical surface. The arrangement of the strip-like protrusion can be referred to the arrangement of the inclined groove, and will not be described in more detail.

For another example, the third composite vibration pattern generating portion may include at least one helical protrusion provided on the outer periphery of the handle 100 at the second predetermined included angle with respect to the handle longitudinal central axis L1. The helical protrusion may extend in the direction of a conical helix, and the second predetermined angle may be a helix angle of the conical helix. The arrangement of the helical protrusion can be referred to the arrangement of the helical groove, and will not be described in more detail.

Of course, the third composite vibration pattern generating portion may alternatively include both at least one strip-like protrusion and at least one helical protrusion, and also enable the cutting portion 310 to realize a composite vibration of the longitudinal vibration and the torsional vibration. When the vibration source 60 generates a longitudinal vibration, part of the longitudinal vibration component of the longitudinal vibration acts on the third composite vibration pattern generating portion. Since the third composite vibration pattern generating portion is at the second predetermined included angle with respect to the handle longitudinal central axis L1, the part of the longitudinal vibration component is converted into the torsional vibration for rotation along the circumferential direction of the conical transition section, so as to drive the cutting portion 310 to realize the torsional vibration. Moreover, since there is still part of the longitudinal vibration component that is not converted to the torsional vibration, the cutting portion 310 can still generate a longitudinal vibration under the action of the vibration source 60. That is, the cutting portion 310 of the blade 300 can realize a composite vibration of the longitudinal vibration and the torsional vibration.

It can be understood that the structure and function of the third composite vibration pattern generating portion are similar to those of the first composite vibration pattern generating portion 410, and reference may be made specifically to the first composite vibration pattern generating portion 410. The composite vibration pattern generating portion 400 may include at least one of the first composite vibration pattern generating portion 410, the second composite vibration pattern generating portion 420 and the third composite vibration pattern generating portion, which may be selected according to a desired vibration mode.

In some embodiments, the vibration source 60 includes an ultrasonic transducer. The ultrasonic transducer may be connected to the first end of the handle 100, and can generate a longitudinal vibration and/or a torsional vibration.

It can be understood that in the above various embodiments, description is made by only taking an example in which the ultrasonic transducer generates a longitudinal vibration, and the composite vibration of the cutting portion 310 is realized mainly by a change in the structure of the medical ultrasonic scalpel 10. In other embodiments, the ultrasonic transducer may enable a torsional motion and convert the torsional motion into a composite vibration including the torsional vibration by a change in the structure of the medical ultrasonic scalpel 10.

Figure 23:
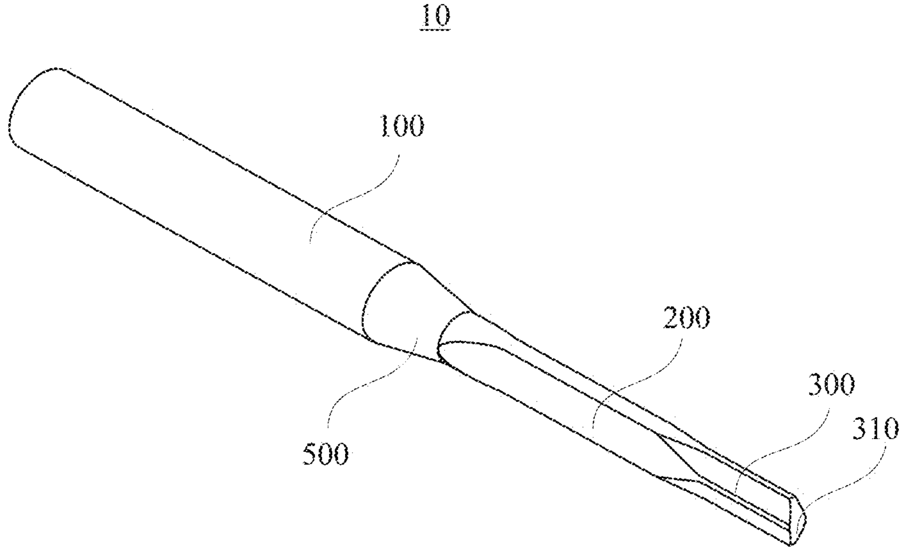
FIG. 23 shows a schematic structural diagram of a medical ultrasonic scalpel according to yet another embodiment of the present application.
Figure 24:
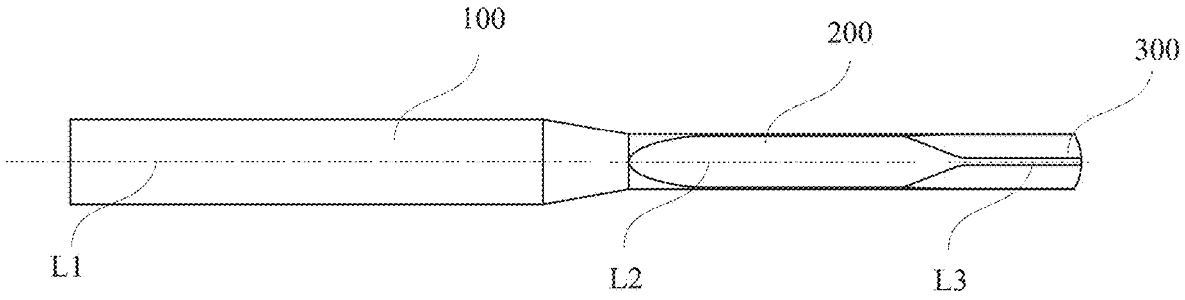
FIG. 24 is a front view of the medical ultrasonic scalpel of FIG. 23.
Figure 25:
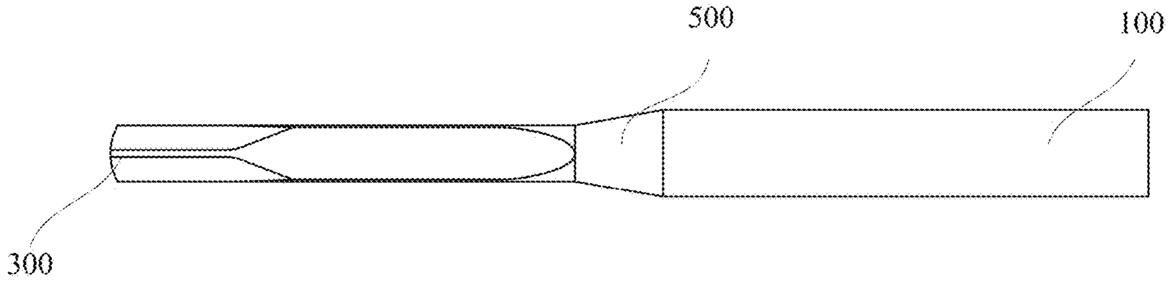
FIG. 25 is a rear view of the medical ultrasonic scalpel of FIG. 23.
Figure 26:
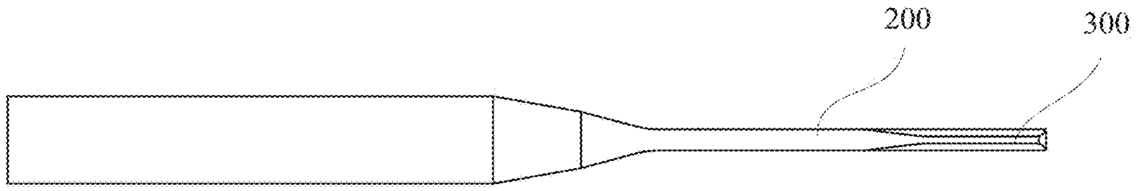
FIG. 26 is a top view of the medical ultrasonic scalpel of FIG. 23.
Figure 27:
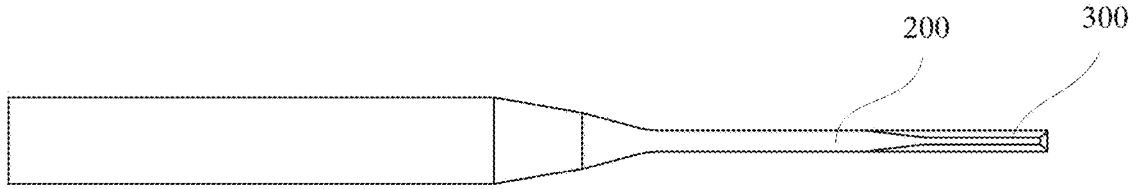
FIG. 27 is a bottom view of the medical ultrasonic scalpel of FIG. 23.
Figure 28:
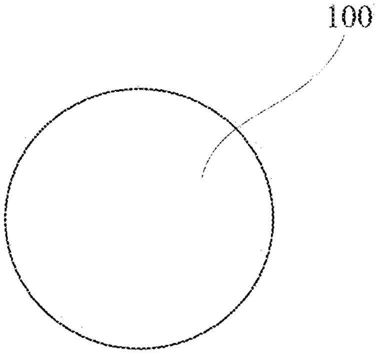
FIG. 28 is a left side view of the medical ultrasonic scalpel of FIG. 23.
Figure 29:
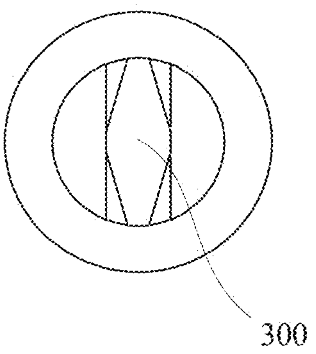
FIG. 29 is a right side view of the medical ultrasonic scalpel of FIG. 23.

FIG. 23 shows a schematic structural diagram of a medical ultrasonic scalpel according to yet another embodiment of the present application; FIG. 24 is a front view of the medical ultrasonic scalpel of FIG. 23; FIG. 25 is a rear view of the medical ultrasonic scalpel of FIG. 23; FIG. 26 is a top view of the medical ultrasonic scalpel of FIG. 23; FIG. 27 is a bottom view of the medical ultrasonic scalpel of FIG. 23; FIG. 28 is a left side view of the medical ultrasonic scalpel of FIG. 23; and FIG. 29 is a right side view of the medical ultrasonic scalpel of FIG. 23.

Referring to FIGS. 22 to 29, in this embodiment, the ultrasonic transducer may generate a longitudinal vibration and a torsional vibration, and at least a part of the handle 100 and the shank 200 constitutes the composite vibration pattern generating portion. In this embodiment, no special modification is made to the structure of the medical ultrasonic scalpel 10, and the longitudinal vibration and the torsional rotation, i.e. the composite vibration, of the cutting portion 310 are realized by virtue of a variety of vibrations generated by the ultrasonic transducer.

Of course, in some other embodiments, the ultrasonic transducer may simultaneously generate a torsional vibration and a longitudinal vibration, and the structure of the medical ultrasonic scalpel 10 may be modified. The composite vibration pattern generating portion 400 may include a second composite vibration pattern generating portion 420, so as to realize a composite vibration including the longitudinal vibration, the torsional vibration and the bending vibration.

It can be understood that the vibration mode of the ultrasonic transducer and the structure of the composite vibration pattern generating portion 400 can be combined according to the requirements, the ultrasonic transducer generates at least one of the torsional vibration and the longitudinal vibration, and the composite vibration pattern generating portion 400 may include at least one of the first composite vibration pattern generating portion 410, the second composite vibration pattern generating portion 420, and the third composite vibration pattern generating portion, to realize a composite vibration of the cutting portion 310.

Figure 30:
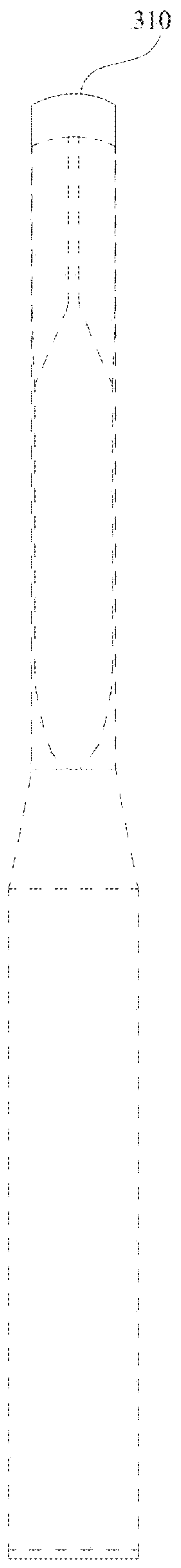
FIG. 30 is a diagram showing the deformation of the medical ultrasonic scalpel according to the embodiment of the present application during longitudinal vibration.

FIG. 30 is a diagram showing the deformation of the medical ultrasonic scalpel according to the embodiment of the present application during longitudinal vibration. Referring to FIGS. 23 and 30, the dotted lines show a state of the medical ultrasonic scalpel 10 before a vibration is generated, and the solid lines show a state when the length of the medical ultrasonic scalpel 10 is increased while a longitudinal vibration is generated. Since the change in the width of the medical ultrasonic scalpel 10 is not significant during the longitudinal vibration, its overall profile is not shown in FIG. 30, but only the part with an increased length is shown. The longitudinal vibration of the medical ultrasonic scalpel 10 makes it possible to realize a bone cutting treatment.

Figure 31:
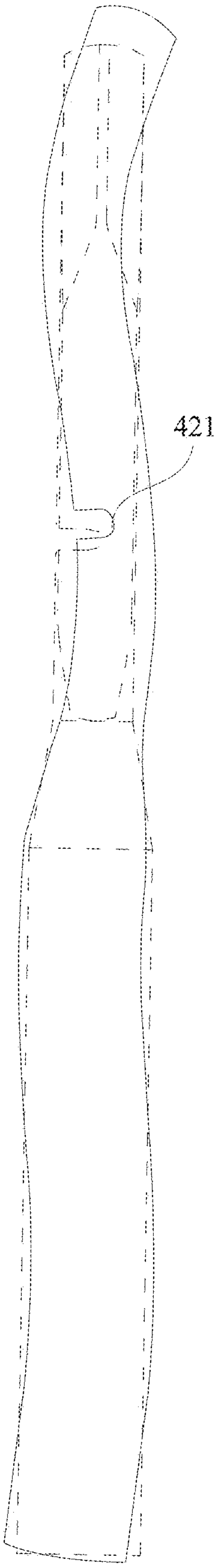
FIG. 31 is a diagram showing the deformation of the medical ultrasonic scalpel according to the embodiment of the present application during bending vibration.
Figure 32:
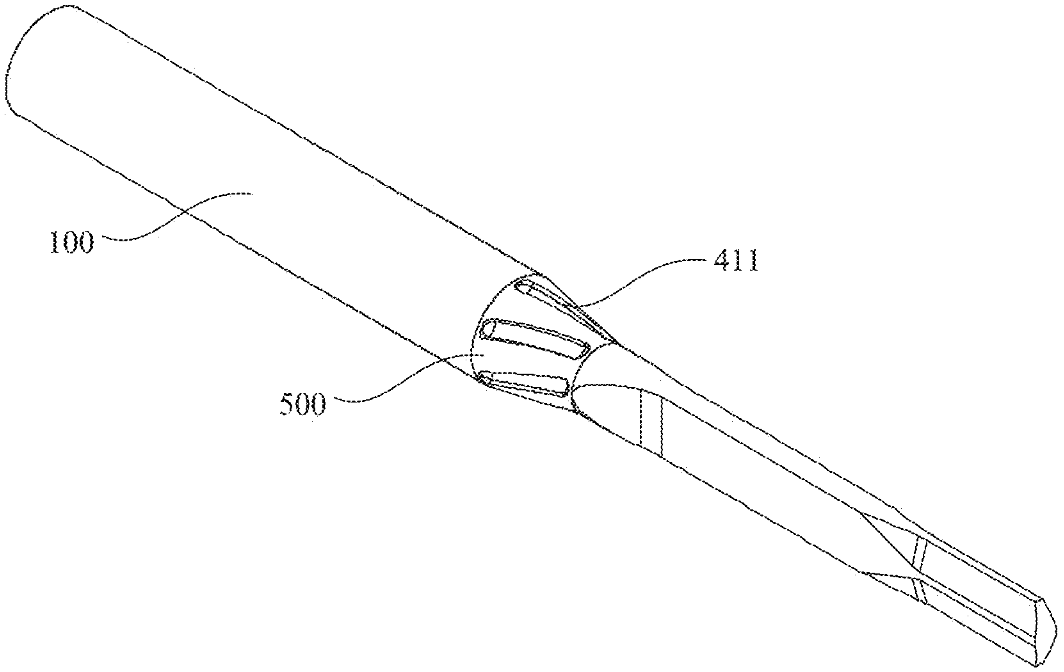
FIG. 32 shows a schematic structural diagram of a medical ultrasonic scalpel according to another embodiment of the present application.

FIG. 31 is a diagram showing the deformation of the medical ultrasonic scalpel according to the embodiment of the present application during bending vibration. Referring to FIGS. 9 and 31, the dotted lines show a state of the medical ultrasonic scalpel 10 before a vibration is generated, and the solid lines show a state when the medical ultrasonic scalpel 10 generates a longitudinal vibration. The second composite vibration pattern generating portion 420 can change the longitudinal vibration into a bending vibration, such that the medical ultrasonic scalpel 10 is bent, and the length thereof is increased, that is, the cutting portion 310 generates a composite vibration including the longitudinal vibration and the bending vibration. The medical ultrasonic scalpel 10 can realize bone cutting and grinding treatments.

With continued reference to FIG. 1, an embodiment of the present application also provide a medical ultrasonic scalpel system, including a vibration source 60 and a medical ultrasonic scalpel 10. The vibration source 60 is connected to a first end of a handle 100 of the medical ultrasonic scalpel 10, and the vibration source 60 is configured to generate a vibration.

The structures and functions of the vibration source 60 and the medical ultrasonic scalpel 10 are the same as those in the above various embodiments and will not be described in more detail herein, and reference may be made specifically to the above various embodiments.

The medical ultrasonic scalpel system provided in this embodiment enables the medical ultrasonic scalpel to generate a variety of vibrations to adapt to various types of surgeries, thereby improving the scope of application of the medical ultrasonic scalpel in surgery.

An embodiment of the present application also provides a robotic-assisted ultrasonic scalpel system, including: a robotic-assisted surgical device and a medical ultrasonic scalpel system. The robotic-assisted surgical device is connected to a medical ultrasonic scalpel of the medical ultrasonic scalpel system to control movement of the medical ultrasonic scalpel.

The structure and function of the medical ultrasonic scalpel system are the same as those in the above various embodiments and will not be described in more detail herein, and reference may be made specifically to the above various embodiments. The robotic-assisted surgical device may include a robot capable of moving in multiple degrees of freedom, and precise control of the surgery can be realized by operating the medical ultrasonic scalpel by the robot.

It should be understood that, in this description, the orientations or positional relationships or dimensions denoted by the terms, such as “center”, “longitudinal”, “transverse”, “length”, “width”, “thickness”, “upper”, “lower”, “front”, “rear”, “left”, “right”, “vertical”, “horizontal”, “top”, “bottom”, “inner”, “outer”, “clockwise”, “counterclockwise”, “axial”, “radial” and “circumferential”, are the orientations or positional relationships or dimensions shown on the basis of the drawings, and these terms are used merely for ease of description, rather than indicating or implying that the device or element referred to must have particular orientations and be constructed and operated in the particular orientations, and therefore should not be construed as limiting the scope of protection of the present application.

In addition, the terms such as “first”, “second” and “third” are merely for descriptive purposes and should not be construed as indicating or implying relative importance or implicitly indicating the number of technical features indicated. Thus, the features defined with “first”, “second” and “third” may explicitly or implicitly include one or more features. In the description of the present application, the term “plurality of” means two or more, unless specifically and specifically limited otherwise.

In the present application, unless expressly stated or limited otherwise, the terms such as “mounting”, “connection”, “connected” and “fixing” should be interpreted broadly, for example, either fixed or detachable connection, or integration; may be a mechanical connection, or an electrical connection, or communication; and may be a direct connection or an indirect connection by means of an intermediate medium, or may be internal communication between two elements or interaction between the two elements. For those of ordinary skills in the art, the specific meaning of the terms mentioned above in the present application may be construed according to specific circumstances.

In the present application, unless expressly stated or limited otherwise, the expression of the first feature being “above” or “below” the second feature may include the case where the first feature is in direct contact with the second feature, and may also include the case where the first and second features are not in direct contact but are contacted via another feature therebetween. Furthermore, the first feature being “over”, “above” or “on” the second feature includes the case where the first feature is directly or obliquely above the second feature, or merely indicates that the first feature is at a higher level than the second feature. The first feature being “below”, “under” or “beneath” the second feature includes the case where the first feature is directly or obliquely below the second feature, or merely indicates that the first feature is at a lower level than the second feature.

This description provides many different embodiments or examples that can be used to implement the present application. It should be understood that these various embodiments or examples are purely illustrative and are not intended to limit the scope of protection of the present application in any way. On the basis of the disclosure of the description of the present application, those skilled in the art will be able to conceive of various changes or substitutions. Any changes or substitutions shall fall within the scope of protection of the present application. Therefore, the scope of protection of the present application shall be subject to the scope of protection of the claims.

The invention claimed is:

1. A medical ultrasonic scalpel, comprising:

a handle having a handle longitudinal central axis, a first end of the handle being configured to be connected to a vibration source to receive a vibration generated by the vibration source;

a shank having a shank longitudinal central axis, a first end of the shank being connected to a second end of the handle opposite to the first end of the handle;

a blade having a blade longitudinal central axis, a first end of the blade being connected to a second end of the shank opposite to the first end of the shank, and a second end of the blade being provided with a cutting portion for cutting a tissue to be cut; and a composite vibration pattern generating portion provided on at least one of the handle and the shank and configured to convert the vibration received from the vibration source into a composite vibration of the cutting portion of the blade, the composite vibration comprising at least two of the following vibrations:

a longitudinal vibration parallel to at least one of the handle longitudinal central axis, the shank longitudinal central axis and the blade longitudinal central axis;

a torsional vibration with at least one of the handle longitudinal central axis, the shank longitudinal central axis and the blade longitudinal central axis as a torsional central axis; and a bending vibration laterally offset from at least one of the handle longitudinal central axis, the shank longitudinal central axis and the blade longitudinal central axis;

the composite vibration pattern generating portion further comprising a bending vibration pattern generating portion provided in the handle or the shank and configured to convert a longitudinal vibration component of the vibration source into the bending vibration;

the bending vibration pattern generating portion being formed by at least one lateral cutout of the handle or the shank; or the bending vibration pattern generating portion being formed by at least one lateral projection of the handle or the shank.

2. The medical ultrasonic scalpel according to claim 1, wherein the handle longitudinal central axis and the shank longitudinal central axis coincide with each other, and the blade longitudinal central axis is offset by a predetermined distance from, or at a predetermined angle with respect to, the handle longitudinal central axis and the shank longitudinal central axis; or the handle longitudinal central axis and the blade longitudinal central axis coincide with each other, and the shank longitudinal central axis is offset by a predetermined distance from, or at a predetermined angle with respect to, the handle longitudinal central axis and the blade longitudinal central axis; or the handle longitudinal central axis, the shank longitudinal central axis and the blade longitudinal central axis coincide with one another.

3. The medical ultrasonic scalpel according to claim 1, wherein the composite vibration pattern generating portion comprises a first torsional vibration pattern generating portion provided in the handle and configured to convert a longitudinal vibration component of the vibration source into the torsional vibration.

4. The medical ultrasonic scalpel according to claim 3, wherein the first torsional vibration pattern generating portion is at least one inclined groove and/or helical groove provided on an outer periphery of the handle at a first predetermined included angle with respect to the handle longitudinal central axis; or the first torsional vibration pattern generating portion is at least one strip-like protrusion and/or helical protrusion provided on the outer periphery of the handle at the first predetermined included angle with respect to the handle longitudinal central axis.

5. The medical ultrasonic scalpel according to claim 4, wherein the at least one inclined groove and/or helical groove comprises two or more inclined grooves and/or helical grooves evenly distributed along the outer periphery of the handle.

6. The medical ultrasonic scalpel according to claim 3, wherein a transverse dimension of the handle is greater than a transverse dimension of the shank, and the second end of the handle is connected to the first end of the shank via a conical transition section.

7. The medical ultrasonic scalpel according to claim 6, wherein the composite vibration pattern generating portion further comprises a second torsional vibration pattern generating portion provided in the conical transition section and configured to convert a longitudinal vibration component of the vibration source into the torsional vibration.

8. The medical ultrasonic scalpel according to claim 7, wherein the second torsional vibration pattern generating portion is at least one inclined groove and/or helical groove provided on an outer periphery of the conical transition section at a second predetermined included angle with respect to the handle longitudinal central axis; or the second torsional vibration pattern generating portion is at least one strip-like protrusion and/or helical protrusion provided on the outer periphery of the conical transition section at the second predetermined included angle with respect to the handle longitudinal central axis.

9. The medical ultrasonic scalpel according to claim 1, wherein the vibration source comprises an ultrasonic transducer capable of generating a longitudinal vibration and/or a torsional vibration.

10. A medical ultrasonic scalpel system, comprising a vibration source and the medical ultrasonic scalpel of claim 1, the vibration source being connected to the first end of the handle of the medical ultrasonic scalpel and configured to generate a vibration.

11. The medical ultrasonic scalpel system according to claim 10, wherein the handle longitudinal central axis and the shank longitudinal central axis coincide with each other, and the blade longitudinal central axis is offset by a predetermined distance from, or at a predetermined angle with respect to, the handle longitudinal central axis and the shank longitudinal central axis; or the handle longitudinal central axis and the blade longitudinal central axis coincide with each other, and the shank longitudinal central axis is offset by a predetermined distance from, or at a predetermined angle with respect to, the handle longitudinal central axis and the blade longitudinal central axis; or the handle longitudinal central axis, the shank longitudinal central axis and the blade longitudinal central axis coincide with one another.

12. The medical ultrasonic scalpel system according to claim 10, wherein the composite vibration pattern generating portion comprises a torsional vibration pattern generating portion provided in the handle and configured to convert a longitudinal vibration component of the vibration source into the torsional vibration.

13. The medical ultrasonic scalpel system according to claim 10, wherein the vibration source comprises an ultrasonic transducer capable of generating a longitudinal vibration and/or a torsional vibration.

14. A robotic-assisted ultrasonic scalpel system, comprising: a robotic-assisted surgical device and the medical ultrasonic scalpel system of claim 10, wherein the robotic-assisted surgical device is connected to the medical ultrasonic scalpel of the medical ultrasonic scalpel system to control movement of the medical ultrasonic scalpel.

* * * * *